United States Patent [19]

Giampapa

[11] Patent Number: 4,770,662
[45] Date of Patent: Sep. 13, 1988

[54] SENSATE VIBRATORY PROSTHESIS

[76] Inventor: Vincent C. Giampapa, 5 Franklin Ave, Suite G-3, Belleville, N.J. 07103

[21] Appl. No.: 72,950

[22] Filed: Jul. 13, 1987

[51] Int. Cl.$^4$ ............................ A61F 2/48; A61F 2/68
[52] U.S. Cl. ........................................ 623/24; 623/53; 623/57
[58] Field of Search .................................. 623/24–26, 623/27, 53, 57, 64

[56] References Cited

U.S. PATENT DOCUMENTS

| | | | |
|---|---|---|---|
| 2,582,234 | 1/1952 | Conzelman, Jr. et al. | 623/24 X |
| 3,751,733 | 8/1973 | Fletcher et al. | 624/24 |
| 3,820,168 | 6/1974 | Horvath | 624/24 |

FOREIGN PATENT DOCUMENTS 2016295 10/1971 Fed. Rep. of Germany ........ 623/25

Primary Examiner—Ronald L. Frinks
Attorney, Agent, or Firm—Melvin K. Silverman

[57] ABSTRACT

A sensory input discrimination system for use with a prosthetic limb such as a prosthetic hand having five digits. The discrimination system includes pairs of sonic frequency generators in electrical communication with pressure transducers which are disposed proximally to each other and within the extremity of corresponding digits of the prosthetic hand, the frequency generators having discrete sonic frequencies. The electrical communication between each frequency generator and the pressure sensor is open in the absence of contact pressure, and closed in the presence of contact pressure. Such closure generates a discrete sonic frequency output from the digit to which the contact pressure has been applied. In the prosthesis, a power unit amplifies the frequency outputs and provides power for the operation of the frequency generators and pressure transducers. The power unit exhibits an output including a voltage and a sonic frequency. The sonic output signal of the power unit is placed into sonic proximity of a sonic contact in, and vibratory receptors on, a bone stump, both at the amputation site corresponding to the connection of the prosthetic limb. Such receptors will generate neutral impulses having a signal pattern correlative to the sonic output signlas of the power unit, thus producing impulses which will travel from the stump to the posterior columns of the spinal cord and, therefrom, to the brain where discrimination of the impulses generated by the sonic signals will be accomplished to recognize the digit-location of the pressure-related stimuli.

6 Claims, 2 Drawing Sheets

SENSATE VIBRATORY PROSTHESIS

BACKGROUND OF THE INVENTION

The invention relates generally to prosthetics and, more particularly, to a sensing system for placement in the digits of a prosthetic hand or arm.

The prior art contains many examples of prosthetics and, more particularly, to a sensing system for placement in the digits of a prosthetic hand or arm.

The prior art contains many examples of prosthetic sensors adapted to enable the user of the prosthesis to determine the existence of such parameters as pressure, stress or heat upon the digits of the surface of the prosthetic device. See for example U.S. Pat. No. 3,751,733 (1973) to Fletcher entitled Tactile Sensing Means for Prosthetic Limbs. Also, a generalized class of sensors for prosthetic devices exists, the purpose of which is to enable the user to gauge the movement and velocity of the prosthetic limb. In this regard, see U.S. Pat. No. 3,820,168 (1984) to Horvath, entitled System for Operating a Prosthetic limb.

None of the prior art, however, contains any method by which a user of a prosthetic device can determine or differentiate as to which of the digits (in the case of a hand) or area of a given surface of a prosthetic device is, at any particular time, subject to pressure or the like. That is, the prior art does not teach any method by which differentiation between pressure, or relative pressures, between digits or areas of a prosthetic hand or limb, can be achieved.

Further, all prior art known to the inventor pertains to the transmission of signals to the skin covering whatever organs exist at the amputation site. In distinction, the present disclosure transmits a vibrational signal to the bone stump nearest to the amputation site. From that point, neural impulses are transmitted to the posterior columns of the spinal cord and, therefrom, the brain. This represents a different neurologic circuit than is employed by the prior art known to the inventor. Accordingly, this invention reflects an effort to provide a sensor for a prosthetic device in which the wearer will not simply sense pressure, heat or movement in a generalized manner as the prior art teaches, but will be able to determine exactly which digit or which area of the prosthesis is the origin of the sensed parameter.

SUMMARY OF THE INVENTION

The invention constitutes a sensory input location discrimination system for use with a prosthetic limb, such as a prosthetic hand having five digits. The discrimination system includes a plurality of pairs of sonic frequency generators and pressure transducers, the generators and transducers disposed proximally to each other and within the extremity of a corresponding plurality of digits of the prosthesis, the frequency generators having respective and discreet sonic frequencies. The electrical communication between each frequency generator and its pressure sensor are open in the absence of contact pressure and closed in the presence of contact pressure, in which closure of said electrical communication will generate a discreet sonic frequency output from that digit to which contact pressure has been applied. A power unit is in electrical communication with the outputs of the frequency generators and pressure transducers, the power unit amplifying the outputs to provide power for the operation of said frequency generators and pressure transducers, the power unit positioned within the prosthesis, the power unit having an output including a voltage and a sonic frequency. A surgical connection is made of said sonic output signal of said power unit into the sonic proximity of the vibratory receptors of a bone stump at an amputation site corresponding in location to the prosthetic limb. Said receptors will generate a neural impulse, having a signal pattern correlative to the sonic output signal to said power unit, which neural impulses travel from the bone stump to the posterior columns of the spinal cord and, therefrom, to the brain, wherein discrimination of neural impulses generated by correlative signals can be readily accomplished by the brain to thereby recognize the digit location of the pressure, or pressure-related stimulus, to the prosthetic device.

It is accordingly an object of the instant invention to provide a prosthetic device having an improved sensing capability.

It is another object to provide a prosthetic device having sensing units, supported by the digits, having a capability for determining which digit is subject to pressure, or other parameter, at a given time.

A yet further object is to provide a sensing device which will render more meaningful prior art developments in parameter sensing capability in that the user will be able to determine more specifically that part of the prosthesis which is subject to the sensed parameter.

The above and other objects and advantages of the present invention will become apparent from the below-set forth Detailed Description of the Invention, the Drawings, and Claims appended herewith.

DETAILED DESCRIPTION OF THE INVENTION

Figure 1:
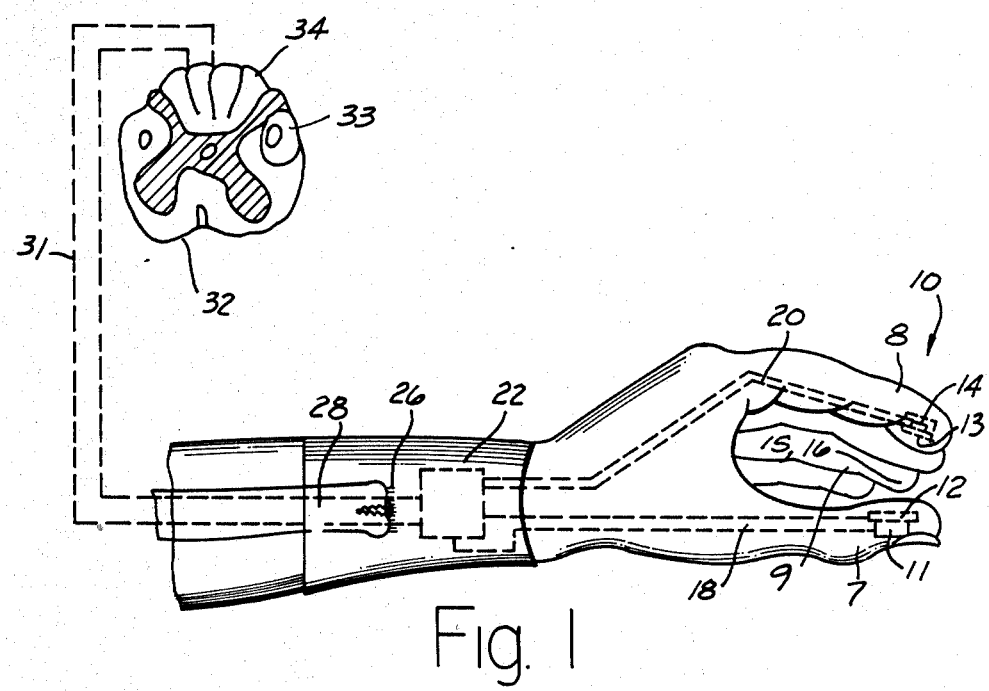
FIG. 1 is a pictorial view of a prosthetic device including therein sonic frequency generators for localizing the location of tactile stimuli with cross section of neural pathing of the posterior column.
Figure 2:
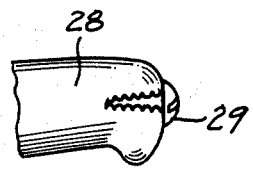
FIG. 2 is an enlarged view of a suitable sonic contact in a bone stump.

Referring now to the drawings wherein like reference characters designate like or corresponding parts, there is illustrated in FIG. 1, an electromechanical prosthesis 10 of any suitable design. Since prosthetic devices, such as an electromechanical hand, are well-known and form no significant part of the instant invention, a detailed description of prosthesis 10 is omitted in the interest of brevity. Rather, it is sufficient to understand that prothesis 10 includes suitable mechanical drive units, not shown, including motors and the like, for driving extented digits (fingers) of the device in reciprocal or reciprocating operation, as is taught by the prior art. Further, it may be understood that prosthesis 10 may, if desired, assume a configuration of a foot, as well as other parts of the anatomy, to which the principals of the present invention may be applied equally as well.

The digits of prosthesis 10 are designated as thumb 7, index finger 8 and end digits 9. Within the distal ends thereof there is, in addition to whatever sensing means may be indicated or used in the prior art (as for example is suggested in the above-referenced U.S. Pat. Nos.

3,751,733 and 3,820,168), provided the instant sensing means, each of which comprises a two-part structure. More particularly, thumb 7 is provided with a pressure transducer 11 and a sonic frequency generator 12. Similarly, index finger 8 is provided with a pressure transducer 13 and a sonic frequency generator 14. Similarly, the end digits 9 are provided with pressure transducers 15 and sonic frequency generators 16 (not shown).

Figure 3:
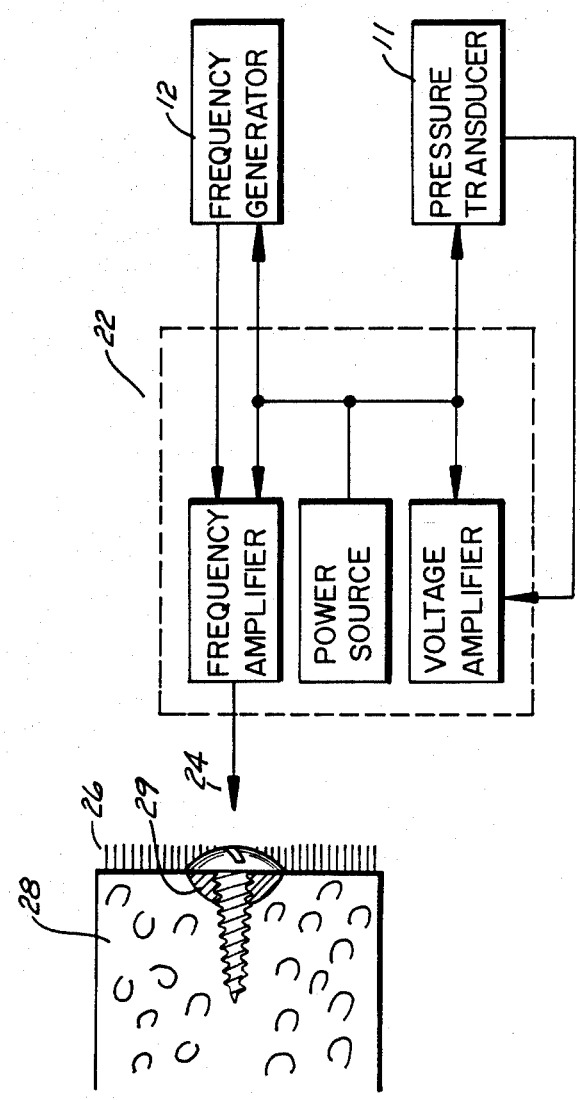
FIG. 3 is a schematic, block diagramatic representation, depicting circuity employed in the vibratory sensate prosthesis.

The said frequency generators, 12, 14, and 16 refer to sonic vibrating elements, the circuit of which (see FIG. 3) is closed upon the application of pressure to the digits. The pressure upon a digit is sensed by the transducers which actuate the sonic frequency generators. In other words, the pressure transducers operate to complete a circuit which will initiate the vibrating of a sonic frequency discreet to the particular digit to which pressure has been applied.

In the study of neurological factors, it has been determined that three represents the optimum number of stimuli which the brain can employ for purposes of differentiation before becoming confused with sensory overload. Bearing this in mind and, as well, to insure reliability in the sensing process, it has been determined that the selected three sonic frequencies should be separated logrithmically, which is to say that each frequency should be at least double the preceeding frequency. Further, it has been found that frequency generator 12 of thumb 7 should employ a frequency of approximately 100 cycles per second; frequency generator 14 of index finger 8 should employ a frequency of 400 cycles per second; and frequency generator 16 for use in end digit should employ a frequency of 700 cycles per second. With this frequency increment for each of the three sensing devices, taken in combination with the limitation to three separate frequencies, it has been found that the brain can easily differentiate between the respective sonic frequencies without sensory overload. Given such discrimination a user of the present system can determine the digit from which pressure, as well as other parametric information such as heat, stress, or motion is originating.

With further reference to FIG. 1, it is seen that the output of said frequency generators and pressure transducers is fed through pathways 18 and 20 from the digits to power unit 22. In the power unit 22 (See FIG. 3), there is provided a power source through which the outputs of such frequency generator and pressure transducers are amplified. The frequency and voltage outputs of power unit 22 are transmitted, through output 24, to the sonic proximity of a sonic contact 29 and vibrating receptors 26 both at the bone stump 28 in the area of the amputation.

It has been, through research found that when said vibrating receptors 26 (as opposed to the skin surrounding the amputation site) are stimulated, neural impulses will travel from said bone stump 28 through nerves 31 to the prosterior columns 34 of the spinal tract 33 and, therefrom, to the brain. See FIG. 1.

In prior art efforts in which stimulation from sensors within the prosthesis are communicated only to the skin, neural impulses reach only the anterior area 32 of the spinal thalamic track 33. Through experimentation it has been determined that the usage of the posterior columns 34 of the spinal track 33 are far superior in terms of the capacity to use the information communicated from sensors in a prosthesis. Accordingly, the methodology of communicating the output 24 of power unit 22 to the vibratory receptors 26 of bone stump 28 is believed to be novel as regards the communication of any type of sensory information from a prosthesis to the brain.

Already documented clinical studies have shown that a user is able to distinguish between the three frequencies above mentioned not only individually but, as well, in combinations of two or three thereof. Further, the learning curve in the use thereof is minimal and it is believed that the present sensate prosthesis will not only make it possible for the user to discriminate between digits receiving stimuli but, as above noted, will permit a more rapid learning process by prosthetic users, in that the sensory end organs in the cutaneous region of the stump have been found to be the more satisfactory transmitter of neurons than is the skin. Accordingly, through the use of completely different anatomical circuit, primary sensory discrimination, not only in the individual digits, but of the specific information generated by the digits within the prosthesis, will be improved.

While there has been shown and described the preferred embodiment of the present invention, it will be understood that the invention may be embodied otherwise than as herein specifically illustrated or described and that within said embodiments certain charges in the detail and construction, and the form of arrangement of the parts may be made without departing from the underlying idea or principles of this invention within the scope of the appended claims.

I claim:

1. A sensory input location discrimination system for use with a prosthetic limb, such as a prosthetic hand having five digits, the discrimination system comprising:

(a) a plurality of pairs of (i) sonic frequency generators and, in electrical communication with said frequency generators, (ii) pressure transducers, said generators and transducers disposed proximally to each other within the extremity of a corresponding plurality of digits of said prosthesis, said frequency generators having respective and discreet sonic frequencies, said electrical communication between each of said frequency generators and its corresponding pressure sensor being open in the absence of contact pressure and closed in the presence of contact pressure, wherein closure of said electrical communication will generate a discreate sonic frequency output from that digit to which contact pressure has been applied;

(b) a power unit in electrical communication with the outputs of said frequency generators and pressure transducers, said power unit amplyfing said outputs to provide power for the operation of said frequency generators and transducers, said power unit positioned within said prosthesis, said power unit having an output including voltage and sonic frequency outputs; and (c) means adapted for surgical connection of said sonic output signal of said power unit into sonic proximity of the vibratory receptors of a bone stump at an amputation site corresponding to the area of connection of the prosthetic limb, whereby said receptors will generate a neural impulse having a signal pattern correlative to said sonic output signal to said power unit, which neural impulses will travel from said bone stump to the posterior columns of the spinal cord and, therefrom, to the brain wherein discrimination of neural impulses generated by said correlative sonic signals can be readily accomplished by the brain to thereby recognize the digit location of the pressure or pressure-related stimulus to the prosthetic device.

2. A system as recited in claim 1 in which said discreet frequencies of said sonic frequency generators of said plurality of pairs of sonic frequency generators and pressure transducers comprise a sequence of increasing frequencies.

3. The system as recited in claim 2 in which the number of said increasing sonic frequencies comprises three.

4. The system as recited in claim 3 in which said sequence of three frequencies comprises the frequencies of 100, 400, and 700 cycles per second.

5. The system as recited in claim 4 in which:
(a) said 100 cycles sonic frequency generator is disposed within the thumb of said prostetic hand;
(b) said 400 cycle sonic frequncy generator is disposed within the index finger of the prosthetic hand; and
(c) said 700 cycle sonic frequency generator is disposed within each of the other three digits of the prosthetic hand.

6. The method of providing sensory input location discrimination to the user of a prosthetic device, comprising the steps of:
(a) providing a plurality of pairs of sonic frequency generators and pressure transducers to areas of the prosthetic device where occasional input sensory discrimination is desired;
(b) assigning a discreet and different sonic frequency to each of said generators of each of said pairs;
(c) providing power and amplification means to the outputs of said pairs; and
(d) surgically connecting amplified outputs of said pairs to the sonic proximity of the vibratory receptors of a bone stump associated with an amputation site related to said prosthetic device, whereby said receptors will generate neural impulses, having a signal patterns correlative to said amplified outputs of said pairs, causing said neural impulses to travel from said bone stump to the posterior columns of the spinal cord and, therefrom, to the brain, in which discrimination of neural impulses generated by such correlative sonic signals can be readily achieved by the brain to thereby relate the digit or other location of a pressure contact,or pressure contact related parameter, to particular surfaces of the prosthetic device.

* * * * *